United States Patent [19]

Korsatko-Wabnegg et al.

[11] Patent Number: 5,128,144
[45] Date of Patent: Jul. 7, 1992

[54] PRESSING HAVING SUSTAINED RELEASE OF ACTIVE COMPOUND

[75] Inventors: Brigitta Korsatko-Wabnegg; Werner Korsatko, both of Graz, Austria

[73] Assignee: PCD Polymere Gesellschaft m.b.H., Schwechat-Mannsworth, Austria

[21] Appl. No.: 587,841

[22] Filed: Sep. 25, 1990

[30] Foreign Application Priority Data

Oct. 16, 1989 [AT] Austria ............................. 2367/89

[51] Int. Cl.$^5$ ..................... A61K 9/20; A61K 9/22; A61K 9/28; A61K 9/30
[52] U.S. Cl. ..................... 424/464; 424/422; 424/426; 424/465; 424/468; 424/474; 424/475; 514/960; 514/962; 514/964
[58] Field of Search ............... 424/422, 426, 464, 465, 424/468, 474, 475; 514/960, 962, 964

[56] References Cited

U.S. PATENT DOCUMENTS

| | | | |
|---|---|---|---|
| 3,773,919 | 11/1973 | Boswell et al. | 424/486 |
| 4,491,575 | 1/1985 | Korsatko | 424/78 |
| 4,786,598 | 11/1988 | Lafferty et al. | 435/146 |
| 4,859,763 | 8/1989 | Takayanagi et al. | 424/426 |
| 4,902,516 | 2/1990 | Korsatko et al. | 424/497 |

FOREIGN PATENT DOCUMENTS

| | | |
|---|---|---|
| 383270 | 6/1987 | Austria . |
| 0058481 | 8/1982 | European Pat. Off. . |
| 0092918 | 11/1983 | European Pat. Off. . |
| 0108882 | 5/1984 | European Pat. Off. . |
| 0133988 | 3/1985 | European Pat. Off. . |
| 0164571 | 12/1985 | European Pat. Off. . |
| 0168862 | 1/1986 | European Pat. Off. . |
| 0172412 | 9/1987 | European Pat. Off. . |
| 0315875 | 11/1987 | European Pat. Off. . |
| 0263490 | 4/1988 | European Pat. Off. . |
| 2051580 | 5/1971 | Fed. Rep. of Germany . |
| 3410380 | 10/1985 | Fed. Rep. of Germany . |
| 3417576 | 11/1985 | Fed. Rep. of Germany . |
| 3636209 | 4/1988 | Fed. Rep. of Germany . |
| 3701625 | 8/1988 | Fed. Rep. of Germany . |
| 3712095 | 10/1988 | Fed. Rep. of Germany . |
| 78/00011 | 12/1978 | PCT Int'l Appl. . |
| 2209937 | 6/1989 | United Kingdom . |

OTHER PUBLICATIONS

"Sci. Pharm.", 57 317-323 (1989).
"Chem. Abst.", 105:11939a (1986).
"Chem. Abst.", 104:193199u (1986).
"Chem. Abst.", 102:209284q (1985).
"Chem. Abst.", 110:219007f (1989).

*Primary Examiner*—Thurman K. Page
*Assistant Examiner*—Carlos Azpuru
*Attorney, Agent, or Firm*—Wenderoth, Lind & Ponack

[57] ABSTRACT

Pressing having sustained release of active compound for the oral or parenteral administration of medicaments, which contains at least one solid pharmaceutical active compound, polylactic acid and a homo- or copolymer of D(−)-3-hydroxybutyric acid and processes for its production.

9 Claims, 1 Drawing Sheet

PRESSING HAVING SUSTAINED RELEASE OF ACTIVE COMPOUND

The application relates to a pressing having sustained release of active compound for the oral or parenteral administration of medicaments.

U.S. Pat. No. 3,773,919 describes pharmaceutical depot compositions for parenteral administration which contain a pharmaceutical active compound and the biologically degradable polymer polylactic acid (PLA), polyglycolic acid (PGA) or a copolymer of lactic acid and glycolic acid and which deliver the active compound in a controlled manner over a relatively long period of time. However, these polymers have extensive elastic properties, a high tendency for electrostatic charge and poor flow properties and can therefore only be compressed to give solid medicament forms with great difficulty.

U.S. Pat. No. 4,491,575 describes pressings having sustained release of active compound which consist of poly-D(−)-3-hydroxybutyric acid and a pharmaceutical active compound. Poly-D(−)-3-hydroxybutyric acid has good flow properties and is highly compressible, but has the disadvantage that it is only degraded very slowly in vivo.

It has now unexpectedly been found that PLA becomes outstandingly compressible as a result of addition of a homo- or copolymer of D(−)-3-hydroxybutyric acid (poly-HB) and that the poly-HB in this mixture is degraded much more rapidly in vivo than pure poly-HB.

The present invention therefore relates to a pressing having sustained release of active compound for the oral or parenteral administration of medicaments, which is characterized in that the pressing contains at least one solid pharmaceutical active compound, polylactic acid and a homo- or copolymer of D(−)-3-hydroxybutyric acid.

Figure 1:
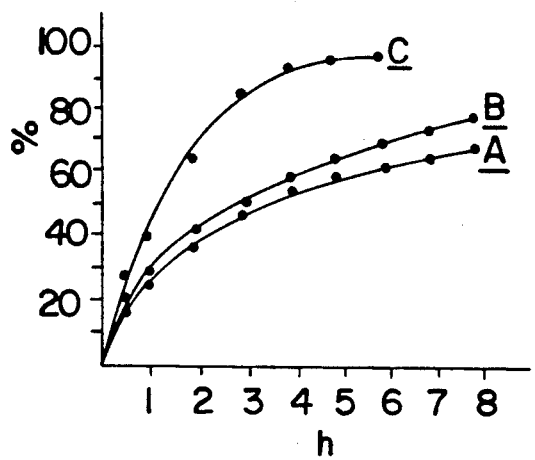
FIGS. 1–5 relate to the amount of active compound released in percent by weight after the respective time (in hours), relative the original amount of active compound in the tablet. For more information, see examples.

Solid pharmaceutical active compounds are in this connection understood as meaning solid pharmaceutical active compounds or mixtures thereof, it being possible for the active compounds to be present in free form or in the form of pharmacologically tolerable salts, in powder form or as granules. The pressing according to the invention contains about 5 to 80 % by weight of active compound.

The polylactic acid used can be present in the form of the racemate or in the form of its enriched or pure enantiomers. It customarily has a molecular weight of about 2,500 to 200,000, preferably a molecular weight of about 3,000 to 150,000 and can be prepared, for example, by the procedures disclosed in U.S. Pat. No. 3,773,919 or GB-A-932,382.

Both homo- and copolymers of D(−)-3-hydroxybutyric acid can be used, homopolymers being preferred. Homopolymers can be prepared, for example, by the procedure described in U.S. Pat. No. 786,598 and copolymers can be prepared by that described in EP-A-0,052,459. The poly-HB customarily used has a molecular weight of about 25,000 to 1,000,000, preferably of 50,000 to 800,000.

PLA and poly-HB are present in the pressing according to the invention in a weight ratio of about 10:90 to 90:10.

The pressings may consist exclusively of active compound, PLA and poly-HB, but it is also possible for them moreover to contain customary pharmaceutical auxiliaries, such as glidants and lubricants, fillers or colorants.

The sustained effect of the pressing according to the invention is dependent on the weight ratio of active compound to polymer, on the weight ratio of PLA to poly-HB, on the molecular weight of the polymers, on the particle size of the constituents and on the manner of production of the pressing. This offers the possibility to the person skilled in the art extremely accurately to adjust controlled release of the active compound over a desired period of time for any active compound and for any desired administration by selection and variation of these parameters.

The invention furthermore also relates to processes for the production of the pressing according to the invention.

For the production of the pressing, at least one solid pharmaceutical active compound in solid, dissolved or suspended form is combined and mixed with solid or dissolved polylactic acid and solid or dissolved homo- or copolymer of D(−)-3-hydroxybutyric acid, after which the solvent or diluent which may be present is evaporated, and the residue is optionally dried, optionally ground and compressed.

According to one embodiment, active compound, PLA and poly-HB are in each case combined in solid form, mixed and compressed. With small amounts, the mixing can be carried out by means of a mortar and pestle or a powder mixing vessel. Large batches can be well mixed with the aid of rotating drums, paddle mixers, plate mixers, mixing screws, ribbon mixers, cone mixers, double-cone mixers and V mixers (twin-shell blenders). The mixtures obtained can be compressed directly without further treatment and with or without further auxiliaries to give tablets, coated tablet cores or other pressings of any desired form and size. The production of the pressings is possible using all conventional tablet presses such as, for example, eccentric presses, rotary presses and hydraulic presses. The compression pressure can be varied over a range from 1 to 10 tonnes, i.e. 98.1–981N per tablet, where the release rate of the active compound is not significantly dependent on the compression pressure in the case of a variation of the compression pressure.

According to a further embodiment, which may preferably be employed for active compounds which are to be administered in high doses, the active compound is initially introduced in solid form into a fluidized bed granulator, for example by the procedure described in U.S. Pat. No. 4,902,516, and is sprayed with a solution of PLA and of poly-HB, dried and compressed. The pressing obtained in this way releases the active compound substantially more slowly in comparison to a pressing which has been obtained by direct compression.

According to another embodiment, the active compound is suspended in a diluent which is simultaneously a solvent for PLA and poly-HB. Such solvents are, for example, halogenated aliphatic hydrocarbons, such as methylene chloride or chloroform. The polymers are added in solid or dissolved form and stirred well with the suspension of the active compound, whereupon the polymers which may have been added in solid form dissolve. The diluent is then evaporated, and the residue is dried, ground and compressed.

According to another embodiment, the active compound is dissolved in a solvent which is simultaneously also a solvent for PLA and poly-HB, and PLA and poly-HB are added in dissolved form. After mixing the solution, the solvent is evaporated, and the residue is dried, ground and compressed.

As a result of the addition of poly-HB to PLA, the known poor processing properties of PLA unexpectedly no longer play any role, even if PLA is present in excess compared to poly-HB. The mixture of PLA and poly-HB shows the good flow properties of poly-HB and can thus also be compressed without addition of any auxiliaries and without problems to give solid medicament forms. The biological degradation of poly-HB only proceeds very slowly in vivo. It has now been found completely unexpectedly that the degradation of poly-HB takes place far more rapidly if, apart from poly-HB, PLA is additionally present in the pressing. In this connection, in vivo degradation studies were carried out in which pressings were implanted subcutaneously in the nape of the neck of mice, removed after a certain period of time and checked for their weight loss, which corresponds to the proportion of polymer degraded. It was shown that poly-HB in mixtures with equal parts by weight of PLA is degraded at least 30 times as rapidly in the body of the experimental animals as poly-HB without addition of PLA.

EXAMPLES

2-Amino-N-(2-(2,5-dimethoxyphenyl)-2-hydroxyethyl)acetamide (midodrine) and N'-(3-acetyl-4-(3-((1,1-dimethylethyl)amino)-2-hydroxypropoxy)phenyl)-N,N'-diethylurea (celiprolol) were selected as active compounds. The molecular weight of the PLA used was 20,325, that of the poly-HB used was 68,170. In each case the particle size fraction from 200 to 315 micrometers was used. The molecular weights were determined by gel chromatography according to B. Trathnigg and C. Jorde, Journal of Chromatography, 385 (1987), page 17.

In order to determine the in vitro release rates of the active compound, the pressings according to the invention were shaken, corresponding to the physiological conditions, in 0.9% strength NaCl solution at 37° C. and 90 rpm in sealable brown glass bottles in an Infors RS-1-T incubation shaker and examined for the amount of active compound released at specified time intervals. The quantitative analytical determination of the active compounds was carried out by spectrophotometry.

EXAMPLE 1

Production of sustained release tablets from midodrine. HCl, PLA and poly-HB by direct compression 10 mg of midodrine HCl were mixed with 50 mg of a mixture of poly-HB and PLA
A) in the ration 3:1
B) in the ratio 1:1 and
C) in the ratio 1:3 in a cone mixer. The mixtures obtained were compressed to give tablets at a compression pressure of 173.5 N/cm². The tablets had a weight of 60 mg, a diameter of 6 mm and a height of 2 mm. The breaking strength was from A) 7.5 kp to C) 3.0 kp.

The amount of midodrine released was determined by spectrophotometry at a wavelength of 289 nm.

The values collated in Table 1, which are shown graphically in FIG. 1 of the drawing, were determined with the aid of the release studies. The values relate in this case to the amount of active compound released in percent by weight after the respective time (in hours), relative to the original total amount of active compound in the tablet.

TABLE 1

| Time (h) | A | B | C |
| --- | --- | --- | --- |
| 0.5 | 18.27 | 20.91 | 26.80 |
| 1 | 24.58 | 28.73 | 39.23 |
| 2 | 36.08 | 41.53 | 63.50 |
| 3 | 48.30 | 50.65 | 83.51 |
| 4 | 55.20 | 58.34 | 93.13 |
| 5 | 55.80 | 64.29 | 93.41 |
| 6 | 60.93 | 69.54 | 95.03 |
| 7 | 64.92 | 73.91 | 96.77 |
| 8 | 68.53 | 77.84 | 97.25 |
| 24 | 97.34 | 99.49 | 99.84 |

EXAMPLE 2

Production of sustained release tablets from celiprolol.HCl, PLA and poly-HB by direct compression A) 150 mg of celiprolol.HCl, 25 mg of poly-HB and 25 mg of PLA (7.5:1.25:1.25)
B) 100 mg of celiprolol.HCl, 50 mg of poly-HB and 50 mg of PLA (5:2.5:2.5)
C) 50 mg of celiprolol.HCl, 75 mg of poly-HB and 75 mg of PLA (2.5:3.75:3.75)

were mixed in a cone mixer. The mixtures obtained were compressed to give tablets at a compression pressure of 195.18 N/cm². The tablets had a weight of 200 mg, a diameter of 8 mm and a height of 4 mm. The breaking strength was 10.5 kp for A), 9.0 kp for B) and 4.0 kp for C).

The amount of celiprolol.HCl released was determined by spectrophotometry at a wavelength of 324 nm.

Figure 2:
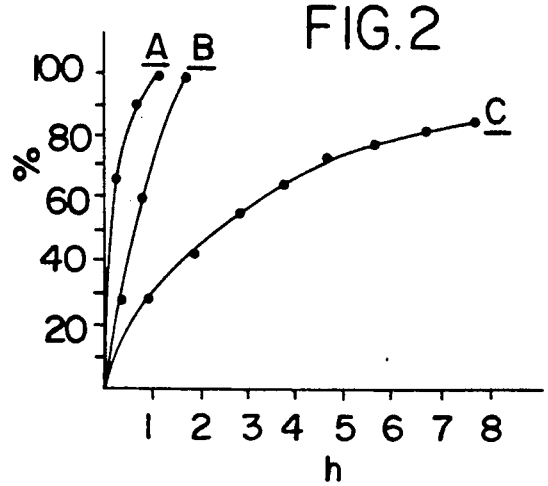

The values collated in Table 2, which are shown graphically in FIG. 2 of the drawing, were determined with the aid of the release studies. The values in this case relate to the amount of active compound released in percent by weight after the respective time (in hours), relative to the original total amount of active compound in the tablet.

TABLE 2

| Time (h) | A (%) | B (%) | C (%) |
| --- | --- | --- | --- |
| 0.5 | 66.64 | 28.24 | 18.89 |
| 1 | 90.37 | 59.82 | 28.53 |
| 1.5 | 100.00 | — | — |
| 2 | — | 99.70 | 42.60 |
| 3 | — | 100.00 | 56.43 |
| 4 | — | — | 65.12 |
| 5 | — | — | 73.33 |
| 6 | — | — | 77.52 |
| 7 | — | — | 81.71 |
| 8 | — | — | 85.95 |
| 24 | — | — | 100.00 |

EXAMPLE 3

Figure 3:
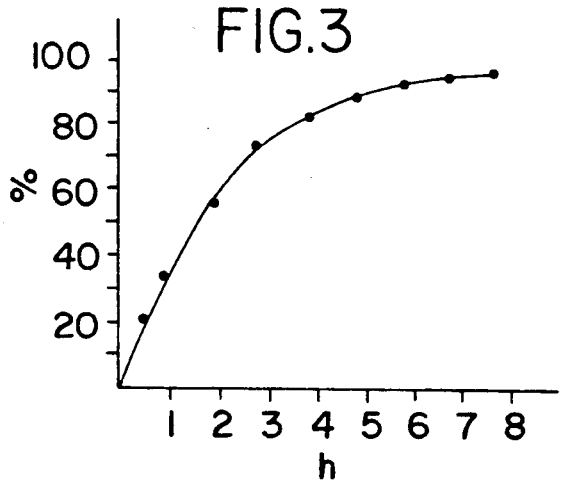

Production of sustained release tablets from celiprolol.HCl, PLA and poly-HB by fluidized bed granulation Celiprolol.HCl granules, obtained by build-up granulation using ethanol were initially introduced into a fluidized bed granulator, Büchi model 710 from Büchi AG, and sprayed with 2% strength solutions of poly-HB and PLA in chloroform and dried. In this way, granules were formed which contained 12% of poly-HB, 12% of PLA and 76% of celiprolol.HCl (1.2:1.2:7.6). The granules were then compressed to give tablets at a compression pressure of 195.18 N/cm$^2$. The tablets had a weight of 250 mg, a diameter of 8 mm and a height of 4 mm. The breaking strength was 19.5 kp, the bulk density 0.45 g/ml and the packing density 0.45 g/ml. The values collated in Table 3, which are shown graphically in FIG. 3 of the drawing, were determined with the aid of the release studies. The values relate in this case to the amount of active compound released in percent by weight after the respective time (in hours), relative to the original total amount of active compound in the tablet.

TABLE 3

| Time (h) | % of active compound released |
| --- | --- |
| 0.5 | 21.18 |
| 1 | 33.19 |
| 2 | 56.60 |
| 3 | 73.34 |
| 4 | 83.13 |
| 5 | 90.62 |
| 6 | 94.61 |
| 7 | 97.11 |
| 8 | 98.38 |

EXAMPLE 4

Figure 4:
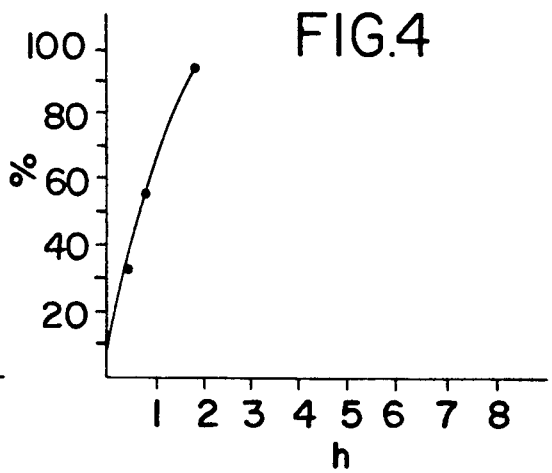

Production of sustained release tablets from celiprolol.HCl, PLA and poly-HB by granulation with the aid of the solvent-evaporation process 10 g of celiprolol.HCl were suspended in 200 ml of chloroform, 1 g each of poly-HB and PLA were added and the mixture was treated in an ultrasonic bath. The suspension was then slowly evaporated to dryness at 40° C in a rotary evaporator. The granules formed were comminuted and sieved. The particle size fraction from 200 to 315 nm was used in order to produce tablets at a compression pressure of 195.18 N/cm$^2$. The tablets contained 84% of celiprolol.HCl, 8% of poly-HB and 8% of PLA. They had a weight of 250 mg, a diameter of 8 mm and a height of 4.3 mm. The breaking strength was more than 20 kp, the bulk density 0.21 g/ml and the packing density 0.31 g/ml. The values collated in Table 4 and shown graphically in FIG. 4 of the drawing were determined with the aid of the release studies. The values relate in this case to the amount of active compound released in percent by weight after the respective time (in hours), relative to the original total amount of active compound in the tablet.

TABLE 4

| Time (h) | Active compound released (%) |
| --- | --- |
| 0.5 | 28.04 |
| 1 | 44.31 |
| 2 | 96.85 |
| 3 | 100.00 |

EXAMPLE 5

Production of sustained release tablets from celiprolol, PLA and poly-HB by granulation with the aid of the solvent-evaporation process 10 g of celiprolol.HCl were dissolved in 100 ml of distilled water and converted into the base by addition of 10 ml of 2N NaOH with stirring. The aqueous phase was extracted several times using chloroform, and the organic phases were combined, dried over sodium sulphate and filtered. 1 g of poly-HB and 1 g of PLA, in each case dissolved in a little chloroform, were then added with stirring to the solution of celiprolol in chloroform prepared in this way. The solvent was evaporated in a rotary evaporator at 40° C., a yellowish oily substance remaining which was dried in a vacuum drying oven to give yellowish white granules. The granules were carefully ground and the particle size fraction from 200 to 315 micrometers was compressed to give tablets at a compression pressure of 195.18 N/cm$^2$ by means of an electrohydraulic press.

Figure 5:
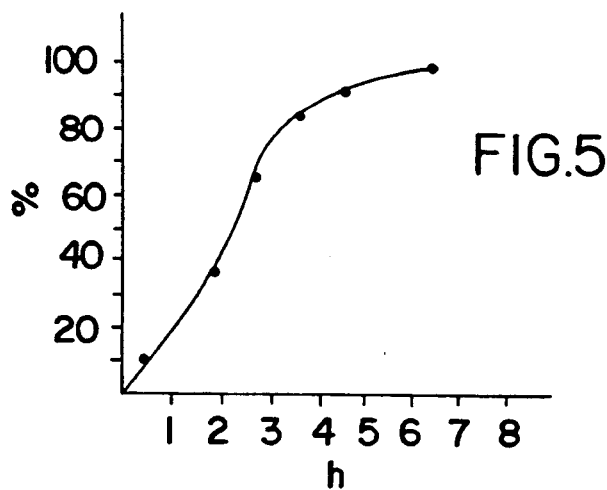

The tablets contained 88.56% of celiprolol, 5.72% of poly-HB and 5.72% of PLA. They had a weight of 250 mg, a diameter of 8 mm and a height of 4.2 mm. The values collated in Table 5 and shown graphically in FIG. 5 of the drawing were determined with the aid of the release studies. The values in this case relate to the amount of active compound released in percent by weight after the respective time (in hours), relative to the original total amount of active compound in the tablet.

TABLE 5

| Time (h) | Active compound released (%) |
| --- | --- |
| 0.5 | 9.07 |
| 1 | 18.64 |
| 2 | 36.49 |
| 3 | 64.48 |
| 4 | 83.89 |
| 5 | 91.79 |

EXAMPLE 6

In-vivo degradation studies
A) poly-HB
B) PLA
C) mixtures of A and B in the weight ratio 1:1
were compressed at a compression pressure of 173.5 N/cm$^2$ to give tablets with a weight of 60 mg, a diameter of 6 mm and a height of 2 mm.

10 tablets each of the compositions A), B) and C) were implanted subcutaneously in the neck crease of mice of the NMRI strain, Biochemie Graz, having a body weight of 20 to 25 g. After 5 weeks, the tablets were removed from the necks, washed, dried to constant weight and the biodegradation of the polymer was measured quantitatively, gravimetrically and by gas chromatography (G. Braunegg, B. Sonnleitner, R. M. Lafferty, European J. Appl Microbiol. Biotechnol. 6, 29–37 (1978)).

The tablets of composition A) were obtained virtually intact after 5 weeks. On average, only 0.2 mg of poly-HB per week had been degraded in the body.

The tablets of compositions B) and C) had been degraded completely and without any residue after 5 weeks. Polymer material was no longer found.

As the tablets of composition C) contained 30 mg of poly-HB, at least 6 mg of poly-HB per week had therefore been degraded in the bodies of the mice.

What we claim is:

1. A pharmaceutical composition for the oral or parenteral administration of medicaments in compressed form having sustained release of active compound comprising at least one solid pharmaceutically active compound, polylactic acid having a molecular weight of about 2,500 to 200,000 and a homo- or copolymer of D(−)-3-hydroxybutyric acid having a molecular weight of about 25,000 to 1,000,000, the polylactic acid: homo- or copolymer of D(−)-3-hydroxybutyric acid weight ratio being from 10:90 to 90:10.

2. The composition according to claim 1, wherein the polylactic acid has a molecular weight of 3,000 to 150,000.

3. The composition according to claim 1, wherein the homo- or copolymer of D(−)-3-hydroxybutyric acid has a molecular weight of 50,000 to 800,000.

4. The composition according to any one of claims 2, 3 and 4, wherein the composition contains 5 to 80 percent by weight of solid pharmaceutically active compound.

5. A process for the production of a pharmaceutical composition for the oral or parenteral administration of medicaments in compressed form having sustained release of active compound comprising combining and mixing at least one solid pharmaceutically active compound in solid, dissolved or suspended form with solid or dissolved polylactic acid having a molecular weight of about 2,500 to 200,000 and solid or dissolved homo- or copolymer of D(−)-3-hydroxybutyric acid having a molecular weight of about 25,000 to 1,000,000, the weight ratio of polylactic acid: homo- or copolymer of (D(−)-3-hydroxybutyric acid being from 10:90 to 90:10, evaporating the solvent or diluent which may be present and compressing the residue with or without drying and grinding before compressing.

6. The process according to claim 5, comprising mixing and compressing at least one solid pharmaceutically active compound with solid polylactic acid and a solid homo- or copolymer of D(−)-3-hydroxybutyric acid.

7. The process according to claim 5, comprising spraying at lease one solid pharmaceutically active compound or granules thereof in a fluidized bed granulator with a solution of polylactic acid and homo- or copolymer of D(−)-3-hydroxybutyric acid, drying and compressing.

8. The process according to claim 5, comprising suspending at least one solid pharmaceutically active compound in a solvent for polylactic acid and for homo- or copolymer of D(−)-3-hydroxybutyric acid, mixing with dissolved polylactic acid and dissolved homo- or copolymer of D(−)-3-hydroxybutyric acid, evaporating the solvent, drying and grinding the residue and compressing.

9. The process according to claim 5, comprising dissolving at least one solid pharmaceutically active compound in a solvent for polylactic acid and for homo- or copolymer of D(−)-3-hydroxybutyric acid, adding and mixing dissolved polylactic acid and dissolved homo- or copolymer of D(−)-3-hydroxybutyric acid, evaporating the solvent, drying and grinding the residue and compressing.

* * * * *